United States Patent [19]

Meyer

[11] 4,203,928
[45] May 20, 1980

[54] PROCESS FOR THE PREPARATION OF 2-NITROBENZALDEHYDE

[75] Inventor: Horst Meyer, Wuppertal, Fed. Rep. of Germany

[73] Assignee: Bayer Aktiengesellschaft, Fed. Rep. of Germany

[21] Appl. No.: 557,296

[22] Filed: Mar. 11, 1975

[30] Foreign Application Priority Data

Mar. 28, 1974 [DE] Fed. Rep. of Germany ....... 2415062

[51] Int. Cl.$^2$ .............................................. C07C 45/18
[52] U.S. Cl. ................................... 568/424; 562/434; 568/939
[58] Field of Search ........................................ 260/599

[56] References Cited

PUBLICATIONS

Cassebaum, Jr.; Pr. Chem. (4) 29(1965), 59–64.
Reissert, Ber. Deut. Chem. Ges, vol. 30 (1897), 1030–1053.
Clarens, Comptes Rendus, vol. 157 (1913), pp. 216–219.
Fieser et al., Reagents for Organic Synthesis (1967), pp. 1083–1087.
Patterson, A German–English Dictionary for Chemists (1959), p. 303.
Webel, A German–English Scientific Dictionary (1930), p. 390.

*Primary Examiner*—Bernard Helfin
*Attorney, Agent, or Firm*—Jacobs & Jacobs

[57] ABSTRACT

2-Nitrobenzaldehyde, a valuable chemical intermediate, is produced by treating the alkali metal salt of a 2-nitrophenylpyruvic acid with an alkali metal hypochlorite in an aqueous medium to produce the corresponding 2-nitrobenzylidene chloride which, upon hydrolysis, yields the desired aldehyde. The 2-nitrophenylpyruvic acid starting material is advantageously prepared through the reaction of a 2-nitrotoluene and a diester of oxalic acid in the presence of an alkali metal alcoholate and can be used directly in the subsequent hypochlorite reaction without isolation. The process is industrially attractive in terms of the overall yield, the availability of starting materials, and the ease of the manipulative steps involved.

9 Claims, No Drawings

PROCESS FOR THE PREPARATION OF 2-NITROBENZALDEHYDE

DETAILED DESCRIPTION

The present invention relates to a new process for the preparation of 2-nitrobenzaldehydes, which can be used, for example, as intermediates for the preparation of the pharmaceutically active 4-nitrophenyl-1,4-dihydropyridine derivatives. The present invention also pertains to the preparation of other intermediate products such as 2-nitrobenzylidene chlorides.

2-Nitrobenzaldehydes have hitherto been extremely difficult to obtain since most of the conventional processes of aldehyde synthesis fail in this case. Thus H. Cassebaum, J. pr. Chem. [4], 29, (1965), noted that while 2-nitrobenzaldehyde has been known for more than 80 years and has occasionally even been manufactured industrially, as for the production of indigo salt T, an advantageous method of preparation of this frequently required substance is still lacking. In L. F. and M. Fieser, Organische Chemie (Organic Chemistry), 2nd edition, Verlag Chemie (1968), page 1004, 2-nitrobenzaldehyde is described as "a very useful starting product for syntheses, which is difficult to obtain by most processes".

The chromic acid oxidation of 2-nitrotoluene in acetic anhydride, reported in Organic Syntheses Coll. Vol. III, page 641, gives very low yields, on the order of 17%, and suffers from the further disadvantages of the required reaction volumes being large and tarry, smeary by-products, which are difficult to isolate, are produced.

Cassebaum, supra, also noted that numerous methods of preparation of 2-nitrobenzaldehyde use 2-nitrobenzyl chloride or 2-nitrobenzyl bromide as starting material, but these starting materials are also difficult to obtain. Thus 2-nitrotoluene reacts with chlorine in the presence of iodine only in glass vessels which transmit UV, to give 2-nitrobenzyl chloride in a yield of only 15%.

2-Nitrobenzylidene chloride, which would be substantially more suitable for the preparation of 2-nitrobenzaldehyde is not obtainable by direct chlorination of 2-nitrotoluene and instead has hitherto only been prepared from the aldehyde itself with phosphorus pentachloride (Kliegl, Ber. dtsch, chem. Ges. 40, 4939 (1907).

2-Nitrotoluene can be reacted with bromine in radical form, such as bromine in the presence of UV light, or with N-bromosuccinimide to give 2-nitrobenzyl bromide, in 45–60% yield; see e.g. H. Cassebaum, Z. Chem. 1969, 340 and Organic Syntheses Vol. 46, 81 (1966). However, these methods cannot be utilized satisfactorily on an industrially scale. Dihalogenation was not observed even under these drastic conditions.

2-Nitrobenzylidene bromide has been obtained reportedly in 33% yield, by reaction of 2-nitrophenylpyruvic acid and sodium hypobromite solution; see A. Reissert, Ber. dtsch. chem. Ges. 30, 1030 (1897). Apart from the low yield which was reported, which when rechecked has been found to be considerably lower still, this method has the disadvantage of a large reaction volume.

While 2-nitrobenzyl bromide can be converted to 2-nitrobenzaldehyde by a Krohnke reaction, the expensive N-bromosuccinimide and the carcinogenic 4-nitrosodimethylaniline are involved, see Org. Syn. 46, 81 (1966). Furthermore, this Krohnke process comprises numerous reaction stages.

Side-chain nitration of 2-nitrotoluene and subsequent oxidation of the 2-nitrophenylnitromethane with potassium permanganate has also been reported to yield 2-nitrobenzaldehyde, see Cassebaum, supra. However, only 10% of theory of 2-nitrophenylnitromethane, the key intermediate, is obtained from 2-nitrotoluene by this process, so that this approach is also industrially uninteresting.

The nitration of cinnamic acid ethyl ester, reported in J. Chem. Soc. (London) 1950, 204, produces an isomer mixture of 2- and 4-nitrocinnamic acid ethyl ester, which can only be separated with difficulty. Saponification of the ester to nitrocinnamic acid and, after separation of the isomers, oxidation with potassium permanganate then gives the aldehyde. In addition to the expensive separation of the isomers and the low yield implicit therein, the large reaction volume again militates against the industrial use of this synthesis of 2-nitrobenzaldehyde.

The large number of methods previously investigated in order to obtain the very valuable 2-nitrobenzaldehyde and the poor yields and results of these methods, show clearly that no industrially satisfactory process is currently available.

According to the present invention, 2-nitrobenzaldehydes are prepared by reacting an alkali metal salt of a 2-nitrophenylpyruvic acid with an aqueous solution of an alkali metal hypochlorite and hydrolyzing the resulting 2-nitrobenzylidene chloride at a temperature of from 20° to 150° C. in the presence of water.

Also provided in accordance with this invention is a process for the preparation of a 2-nitrobenzylidene chloride in which 2-nitrophenylpyruvic acid is treated in an aqueous alkaline medium with an alkali metal hypochlorite solution. Advantageously, the 2-nitrophenylpyruvic acid can be prepared by treating 2-nitrotoluene with a diester of oxalic acid and then used directly without isolation. The nature of the diester of oxalic acid is not critical and generally it is of the formula $(COOR)_2$ in which R is lower alkyl or aralkyl.

It is distinctly surprising that 2-nitrobenzaldehydes can be obtained in such good yields and such high purity in accordance with the process of this invention, since it would be expected from the state of the art that dihalogenation of 2-nitrotoluene would not occur or would at most occur only with very poor yields. Equally surprising is the fact that the reaction of 2-nitrophenylpyruvic acid and sodium hypochlorite produces the 2-nitrobenzylidene chloride in such high yields, since Reissert, supra, was only able to isolate a solid of melting point 160° C. from the reaction of 2-nitrophenylpyruvic acid with calcium hypochlorite. Parenthetically it can be noted that while the ascribed the structure of a dinitrobenzyl diketone to this solid, it later proved to be dinitrodesoxybenzoin; see P. Ruggli and A. Dinger, Helv. Chim. Acta 22, 908 (1939). In any event, the 2-nitrobenzlidene chloride was not produced and conversely, dinitrodesoxybenzoin has not been observed in the case of the present invention.

The processes according to the invention have a number of advantages. Thus the 2-nitrotoluenes and oxalic acid diesters used as starting products are conveniently and readily accessible and in adequate quantity. The end product is obtained from the hydrolysis in high yield and high purity. The preparations of the 2-nitrophenylpyruvic acid and the subsequent preparation of the 2-nitrobenzylidene chloride can be conducted without isolation of the 2-nitrophenylpyruvic acid, so that the process is technically easy to carry out. Finally, 60% of the oxalic acid diester employed can be recovered in the form of dialkali metal oxalate in the hypochlorite reaction stage and this oxalate can be reconverted to the ester without difficulty.

If 2-nitrotoluene, oxalic acid dimethyl ester and sodium methylate are used as starting materials, the course of the reaction can be represented by the following equation:

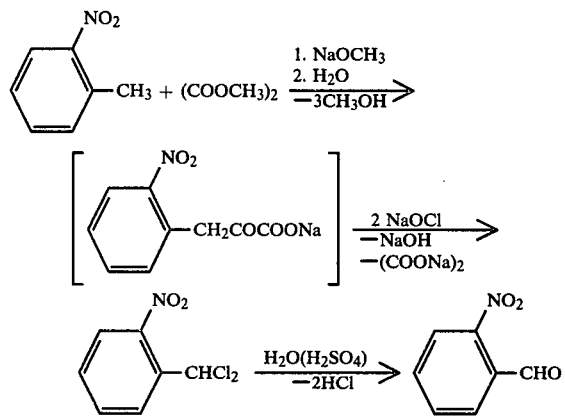

2-Nitrotoluene, diesters of oxalic acid and all other reagents are known or can be prepared according to known methods. The cation of the alcoholates or alkoxides, the 2-nitrophenylpyruvates and the hypochlorites, is shown as sodium but can be any alkali metal such as lithium, sodium or potassium. Sodium or potassium is preferred. Similarly the oxalic acid diester can be of the general formula $(COOR)_2$ in which R is alkyl of from 1 to 6 carbon atoms, especially methyl, ethyl, propyl, isopropyl, butyl, tert.-butyl, pentyl and hexyl, or aralkyl, such as benzyl. The group R does not enter into the basic reaction and can thus be selected solely on the basis of convenience.

The hypochlorite reaction is carried out in an aqueous medium and the 2-nitrobenzylidene chloride is isolated by extraction with a water-immiscible solvent. Preferably however the process is carried out directly in a two-phase system, utilizing water and a water-immiscible solvent for 2-nitrobenzylidene chloride, as for example toluene/water. The 2-nitrobenzylidene chloride is then obtained by merely separating the organic phase and working it up as by distillation.

The hydrolysis of the 2-nitrobenzylidene chloride can be carried out in an alkaline medium, but preferably is carried out under acidic conditions utilizing aqueous organic and inorganic acids. Most preferably the reaction is carried out with sulphuric acid of 50-98% strength, by weight $H_2SO_4$, especially 85-95%. The reaction is carried out at temperatures of about 20° to about 150° C., preferably 60° to 80° C.

In carrying out the hypochlorite reaction, from about 2 to about 3.5 mols of alkali metal hypochlorite are employed per mol of the alkali metal salt of 2-nitrophenylpyruvic acid. The temperature will usually be between about −5 and about +50° C., preferably between 0° and 20° C.

The reactions can be carried out under normal pressure and also under elevated pressure. Preferably, pressures of between 1 and 2 atmospheres are utilized, especially in the case of the hydrolysis reaction step. The resulting 2-nitrobenzaldehyde is collected and purified by conventional means, as for example use of sodium bisulfite, and is thus provided in extremely high purity, e.g. greater than 99%. As noted above, this material can be used, inter alia, as an intermediate for the preparation of coronary-dilating and peripheral-dilating compounds which lower the blood pressure; see, e.g., German Offenlegungsschrift 1,670,827. Thus for example the reaction of 2-nitrobenzaldehyde with β-dicarbonyl compounds and amines produces pharmacologically active 1,4-dihydropyridines.

The following examples will serve to further typify the nature of the present invention without being a limitation on the scope thereof, the invention being defined only by the appended claims.

EXAMPLE 1

144 g (2.67 mols) of sodium methylate are dissolved in 570 ml of ethanol and a mixture of 365 g (2.5 mols) of oxalic acid diethyl ester and 395 g (2.88 mols) of 2-nitrotoluene is poured in at 35° C. The mixture is then briefly heated under reflux and cooled at 65° C., 75 ml of cold water are next added and after addition of a further 640 ml of water (60° C.) the mixture is then boiled under reflux for 1½ hours. A steam distillation is then carried out until two phases no longer pass over. The nitrotoluene from the steam distillate is separated off and recovered by distillation. The residues of the steam distillation are made up to a volume of 3.3 l with water and 150 g of sodium carbonate are dissolved therein. This solution is added dropwise, at 10° C., to a mixture of 1,700 ml of aqueous sodium hypochlorite solution (150 g of NaClO/l) and 60 g of sodium hydroxide in 1,500 ml of water and 1,200 ml of toluene. The mixture is then stirred for a further hour at +10° C. and the solid sodium oxalate is filtered off. The toluene phase is separated from the filtrate and concentrated in vacuo. 279.5 g of 2-nitrobenzylidene chloride, boiling point$_{12\ mm}$ 140° C. are obtained. Yield, 77% of theory, based on 2-nitrotoluene converted. (b) Analogously, 301 g of 2-nitrobenzylidene chloride (82.5%) were obtained starting from 230 g of potassium ethylate, 365 g of oxalic acid diethyl ester and 395 g of 2-nitrotoluene, with 149 g of 2-nitrotoluene being recovered. Yield, 82.5% of theory.

EXAMPLE 2

A solution of 358 g (1.715 mol) of 2-nitrophenylpyruvic acid (melting point 115° C.) and sodium carbonate in water is slowly added dropwise to a mixture of sodium hydroxide solution, sodium hypochlorite solution (162 g of NaClO/l) and 1.35 l of toluene at +10° C. The mixture is stirred for a further hour at +10° C. and the solid (sodium oxalate) is filtered off. The toluene phase is separated from the filtrate. The filter residue is rinsed with 1.35 l of toluene and the aqueous phase is re-extracted therewith. The combined toluene phases are dried with anhydrous sodium sulphate and concentrated in vacuo. 294.5 g (83.5% of theory) of 2-nitrobenzylidene chloride are obtained.

EXAMPLE 3

The stirred volume of two stirring flasks with an overflow totalled 1.05 l. 1,692 ml of an aqueous solution of the Na salt of 2-nitrophenylpyruvic acid (prepared from 163 g of 2-nitrophenylpyruvic acid), 1,692 ml of sodium hypochlorite solution (80 g of NaOCl/l) and 716 ml of toluene were added dropwise per hour (making a total of 4.0 l so that the residence time is 15.7 minutes). The temperature was kept at +10° C. in both flasks by cooling. After starting the continuous operation, 4 l per hour of the issuing reaction mixture are collected in a collecting vessel and worked up as follows:

The mixture was filtered, the phases separated, the aqueous phase extracted with toluene, and the toluene phases were combined, dried with sodium sulphate and concentrated on a rotary evaporator, for 1 hour at 80° C.

After 4 hours' continuous operation, 15.85 l of the 16 l volume employed were recovered. Working up gave 500.0 g = 77.8% of theory of 2-nitrobenzylidene chloride.

EXAMPLE 4

492.5 g (2.39 mols) of 2-nitrobenzylidene chloride in 2 kg of aqueous sulphuric acid (90% strength by weight $H_2SO_4$) are warmed to 70° C. The mixture is stirred until the evolution of hydrogen chloride has ceased, and is then poured onto crushed ice. Thereafter, the mixture is extracted by stirring with 1,300 ml of toluene for 30 minutes, insoluble material is filtered off and the toluene phase is separated from the filtrate. The aqueous phase is re-extracted with toluene. The combined toluene phases are twice extracted by stirring with 20% strength aqueous sodium bisulphite solution. The bisulphite solution is brought to pH 12.5 with sodium hydroxide solution and extracted with toluene. The toluene phase is dried with sodium sulphate and evaporated in vacuo. After 1 hour at 80° C., the residue which remains is 277.5 g (77% of theory) of very pure 2-nitrobenzaldehyde, which on cooling immediately solidifies to crystals. Melting point 42°–43° C.

What is claimed is:

1. The process for the preparation of 2-nitrobenzaldehyde which comprises treating an alkali metal salt of the corresponding 2-nitrophenylpyruvic acid with an alkali metal hypochlorite in an aqueous medium to yield the corresponding 2-nitrobenzylidene chloride and subjecting said 2-nitrobenzylidene chloride to aqueous hydrolysis at a temperature of from about 20° to about 150° C.

2. The process according to claim 1 wherein the alkali metal hypochlorite is sodium hypochlorite.

3. The process according to claim 1 wherein the alkali metal salt of the 2-nitrophenylpyruvic acid is the sodium or potassium salt.

4. The process according to claim 1 wherein said aqueous medium comprises water and a water-immiscible solvent for 2-nitrobenzylidene chloride.

5. The process according to claim 1 wherein from about 2 to about 3.5 mols of the alkali metal hypochlorite are employed per mol of the alkali metal salt of the 2-nitrophenylpyruvic acid.

6. The process according to claim 1 wherein the treatment is conducted at a temperature of from about 0° to about 20° C.

7. The process according to claim 1 wherein the aqueous hydrolysis is conducted in the presence of an acid.

8. The process according to claim 7 wherein the acid is sulphuric acid.

9. The process according to claim 1 wherein the sodium or potassium salt of 2-nitrophenylpyruvic acid is treated with sodium hypochlorite in an aqueous medium comprising water and a water-immiscible solvent for 2-nitrobenzylidene chloride at a temperature of from about 0° to about 20° C. and thereafter subjecting the resultant 2-nitrobenzylidene chloride to hydrolysis in the presence of aqueous acid.

* * * * *